US008869810B2

(12) United States Patent
Pfaffinger et al.

(10) Patent No.: US 8,869,810 B2
(45) Date of Patent: Oct. 28, 2014

(54) CLEANING OR CARE DEVICE FOR MEDICAL INSTRUMENTS

(75) Inventors: Nikolaus Pfaffinger, St. Pantaleon (AT); Christian Spieler, Michaelbeuern (AT)

(73) Assignee: W & H Dentalwerk Bürmoos GmbH, Bürmoos (AT)

( * ) Notice: Subject to any disclaimer, the term of this patent is extended or adjusted under 35 U.S.C. 154(b) by 746 days.

(21) Appl. No.: 13/165,613

(22) Filed: Jun. 21, 2011

(65) Prior Publication Data
US 2011/0315173 A1  Dec. 29, 2011

(30) Foreign Application Priority Data

Jun. 28, 2010  (EP) ..................................... 10167445
Nov. 4, 2010  (EP) ..................................... 10189952

(51) Int. Cl.
*A61C 19/00* (2006.01)
*B08B 3/02* (2006.01)
*A61B 19/00* (2006.01)

(52) U.S. Cl.
CPC ............... *A61C 19/002* (2013.01); *B08B 3/024* (2013.01); *A61B 19/34* (2013.01)
USPC ....................................................... 134/137

(58) Field of Classification Search
CPC ........ B08B 3/02; B08B 3/024; A61C 19/002; A61B 19/34
USPC ........................................................ 134/137
See application file for complete search history.

(56) References Cited

U.S. PATENT DOCUMENTS

| 5,533,539 | A | * | 7/1996 | Sutter et al. | 134/95.2 |
| 5,935,342 | A | * | 8/1999 | Boyd | 134/33 |
| 2006/0185755 | A1 | * | 8/2006 | Vaughn, Jr. | 141/89 |
| 2008/0302393 | A1 | * | 12/2008 | Jafari et al. | 134/22.11 |
| 2009/0188531 | A1 | * | 7/2009 | Boyle et al. | 134/22.11 |
| 2009/0217956 | A1 | * | 9/2009 | Noguchi et al. | 134/57 R |

FOREIGN PATENT DOCUMENTS

WO  WO94/15547  7/1994

OTHER PUBLICATIONS

Machine translation of WO9415547 (Jul. 21, 1994).*

* cited by examiner

*Primary Examiner* — Michael Barr
*Assistant Examiner* — Spencer Bell
(74) *Attorney, Agent, or Firm* — Klarquist Sparkman, LLP

(57) ABSTRACT

A cleaning or care device for medical instruments has a cleaning or care space, at least one connecting device arranged in the cleaning or care space, to which an instrument to be cleaned can be connected, a delivery device for delivery of at least one cleaning or care medium, wherein the delivery device has a frame, on which at least one nozzle for dispensing a cleaning or care medium is provided on the outside of the instrument to be cleaned, the frame being movable relative to the at least one connecting device, to follow essentially a longitudinal axis of an instrument connected to the at least one connecting device, and a magnetic coupling device, which transfers a driving movement generated outside of the cleaning or care space to the frame to move the frame relative to the at least one connecting device. A method for producing a cleaning or care device is also described.

15 Claims, 3 Drawing Sheets

CLEANING OR CARE DEVICE FOR MEDICAL INSTRUMENTS

CROSS REFERENCE TO RELATED APPLICATION

The present application claims priority from the European Patent Application No. 10167445.5, filed Jun. 28, 2010, now abandoned, and from the pending European Patent Application No. 10189952.4, filed Nov. 4, 2010, which are incorporated herein by reference.

BACKGROUND

1. Field

The present invention relates to a cleaning or care device for medical instruments and a method for manufacturing same.

2. Description of Prior Art

Such a cleaning or care device for medical instruments is known from the patent application WO 94/15547 A1. The cleaning or care device comprises a frame which surrounds the instruments to be cleaned and on which multiple nozzles are provided through which a cleaning or care medium can be sprayed onto the outside of the instruments. To be able to supply the instruments along their total length with the cleaning or care medium, a threaded spindle on which the frame is attached and which is driven by means of a motor is provided so that the frame is movable in relation to the instruments to be cleaned.

The disadvantage of this cleaning or care device is that the threaded spindle is arranged in the cleaning chamber, so that room to accommodate the instruments to be cleaned is lost and/or the volume of the cleaning chamber and thus of the entire cleaning or care device must be enlarged to be able to accommodate a corresponding number of instruments to be cleaned. In addition the threaded spindle interferes with the cleaning of the cleaning chamber.

It is thus one object to create a cleaning or care device for medical instruments having a frame with nozzles, the frame being movable along a longitudinal axis of the instruments to be cleaned but the cleaning or care device does not have the aforementioned disadvantages. In particular the cleaning or care device should be designed so that there is no loss of space for accommodating the instruments to be cleaned or the cleaning of the cleaning or care room is not impaired.

SUMMARY

According to one embodiment a cleaning or care device for medical instruments, in particular for dental instruments, is proposed, comprising a cleaning or care space, at least one connecting device which is arranged in the cleaning or care space and to which an instrument to be cleaned can be attached, a delivery device for delivering at least one cleaning or care medium, wherein the delivery device has a frame on which at least one nozzle for dispensing a cleaning or care medium to the outside of the instrument to be cleaned is provided, wherein the frame is movable relative to the at least one connecting device to follow essentially a longitudinal axis of an instrument connected to the at least one connecting device and a magnetic coupling device, which transfers a driving movement generated outside of the cleaning or care space to the frame for moving the frame in relation to the at least one connecting device.

By providing the magnetic coupling device, no other components for moving the frame are necessary inside the cleaning or care space. Thus the cleaning or care space is available exclusively to receive the instruments to be cleaned in an advantageous manner and no space is lost for accommodating the instruments to be cleaned and the cleaning of the cleaning or care space is facilitated.

Any device which dispenses at least one cleaning medium and/or care medium to a medical instrument, in particular a dental instrument in order to clean it, disinfect, sterilize it, free it of soiling or microorganisms or care for it is considered a cleaning or care device in the sense of the present invention. Cleaning media or care media may include, for example, a fluid, in particular hot or cold water, steam, a disinfectant or sterilizing medium, a gas, for example, compressed air or a lubricant, for example, natural or synthetic lubricating oils.

Medical instruments, in particular dental instruments to be cleaned, are understood to be in particular handpieces and contra-angle handpieces for driving a wide variety of tools, for example, rotary drills, dental plaque or calculus-removing tools, files, saws, reamers, etc., handpieces for dispensing medical materials, for example, fillers or anesthetics, functional handpieces for dispensing light, water or air and non-driven hand instruments, for example, endoscopes and the like.

The delivery device for delivering at least one cleaning medium or care medium includes in addition to the frame other components, for example, one or more lines or channels for a cleaning or care medium, one or more pumps for delivering a cleaning or care medium, one or more valves, throttles, flow metering devices, etc. The cleaning or care medium or media are stored either in containers or receptacles in the cleaning or care device and/or they are supplied to the cleaning or care device from external sources via connections on the cleaning or care device.

The frame is movable relative to the at least one connecting device to follow essentially the longitudinal axis or in the case of an angled instrument, a longitudinal axis of an instrument connected to the at least one connecting device. The frame thus moves longitudinally in the cleaning or care space or along (the length) of the instrument to be cleaned or to be cared for, in particular along the entire instrument or along the entire length of the instrument, so that it is certain that the entire instrument is treated with the cleaning or care medium, in particular essentially uniformly over its entire length. Thus a particularly thorough cleaning or care can be achieved.

Additionally or alternatively, the frame moves in the cleaning or care space along the longitudinal axis of the at least one connecting device or along the extension of the longitudinal axis of the at least one connecting device (extension into the cleaning or care space) so that also a particularly thorough cleaning or care can be achieved.

According to one embodiment, the magnetic coupling device has at least one first magnetic element, which is arranged outside of the cleaning or care space and is connected to a drive device and is magnetically coupled to at least one second magnetic element connected to the frame. In an advantageous manner, the drive for the frame and/or for the movement of the frame is thus also arranged outside of the cleaning or care space. The first magnetic element is also preferably arranged outside of the cleaning or care space so that the first magnetic element and the second magnetic element are separated from one another by a wall of the cleaning or care space. The two magnetic elements are especially preferably arranged directly on or adjacent to the wall of the cleaning or care space, thereby achieving an especially strong magnetic coupling.

To achieve a uniform movement of the frame along its entire movement path, according to one embodiment, the drive device connected to the first magnetic element comprises a linear drive which moves the first magnetic element along a wall of the cleaning or care space. The drive device connected to the first magnetic element is preferably designed as a belt drive.

To stabilize or center the movement of the frame according to one embodiment, a guide device for guiding the frame along the wall of the cleaning or care space is provided on the frame and/or on a wall of the cleaning or care. The guide device is designed, for example, as a geometric shape, in particular as a geometric shape with geometrically complementary elements on the frame and on the wall.

To achieve an easy movement on or along the wall of the cleaning or care space, the frame according to one embodiment has one or more protrusions extending away from the body of the frame, with which the frame glides on a wall of the cleaning or care space.

According to another embodiment, the body of the frame has a through-bore in which an instrument to be cleaned can be accommodated or through which an instrument to be cleaned can be passed, wherein multiple nozzles are arranged on the closed inside wall of the through-bore. This ensures that the instrument to be cleaned is treated thoroughly, uniformly and from all sides with the cleaning medium or care medium.

According to another embodiment, the cleaning or care device has a detection device for detecting a relative movement between the frame and the first magnet element. The detection device preferably includes a magnetic sensor which is movable jointly with the first magnetic element arranged outside of the cleaning or care space and is operatively connected to a magnetic element provided on the frame. The magnetic element provided on the frame may be either the second magnetic element or another magnetic element, i.e., a third magnetic element. The magnetic sensor, for example, a Reed sensor or a Hall sensor is designed to detect the magnetic element provided on the frame, for example, through its magnetic field. A relative movement occurs between the frame and the first magnetic element, for example, when the frame is not moved by the first magnetic element or is not moved jointly with the first magnetic element. In this case the magnetic sensor moves away from the magnetic element provided on the frame until the magnetic sensor does not (any longer) detect the magnet element provided on the frame. In this case the magnetic sensor sends a signal to a control unit which informs the user about the relative movement between the frame and the first magnetic element, for example, by means of an optical or acoustic warning device and/or interrupts or suppresses the operation of the cleaning or care device.

To also be able to clean the inside of an instrument connected to the at least one connecting device, according to one embodiment, the at least one connecting device has a channel which is connected to the delivery device for delivering at least one cleaning or care medium, by which a cleaning or care medium can be conveyed into the interior of an instrument.

According to another embodiment, at least two connecting devices are provided for instruments to be cleaned, these connecting devices being movable in relation to the frame such that only one of the connecting devices is opposite a through-bore in the frame on which the at least one nozzle for dispensing a cleaning or care medium is provided. The at least two connecting devices are especially preferably arranged on a shared base element, which is rotatably arranged in the cleaning or care device. Through these embodiments an especially compact cleaning or care device is created with which at least the external cleaning or care, preferably additionally the internal cleaning or care of the instruments is performed sequentially. The through-bore with the at least one nozzle is designed so that only one instrument can be received therein so that when the frame moves along this instrument only this one instrument can be supplied by the at least one nozzle with the cleaning medium or care medium for the purpose of external cleaning or care.

A method for producing a cleaning or care device is defined in that the cleaning or care device is provided with a magnetic coupling device which transfers a driving movement created outside of the cleaning or care space to the frame to move the frame in relation to the at least one connecting device. The cleaning or care device is preferably provided with at least two connecting devices for instruments to be cleaned which are movable in relation to the frame so that only one of the connecting devices is opposite a through-bore in the frame on which the at least one nozzle is provided for dispensing a cleaning or care medium.

The invention is explained below on the basis of preferred embodiments with reference to the accompanying drawings:

DETAILED DESCRIPTION

Figure 1:
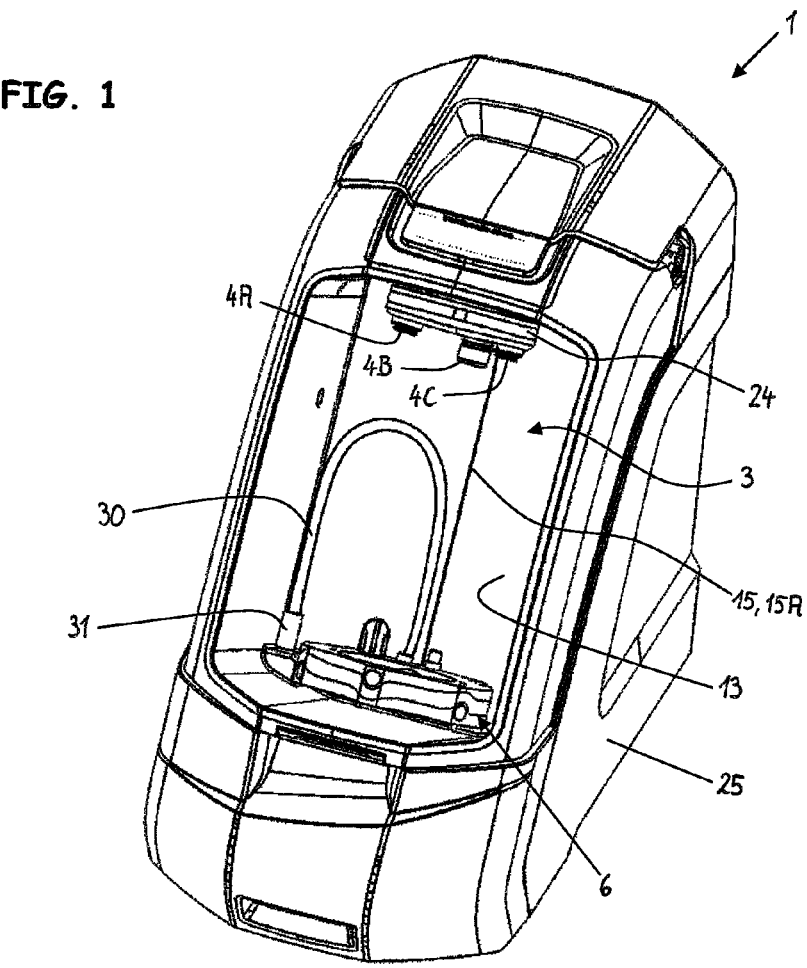
FIG. 1 shows an embodiment of a cleaning and care device with a frame movable by a magnetic coupling device.
Figure 2A:
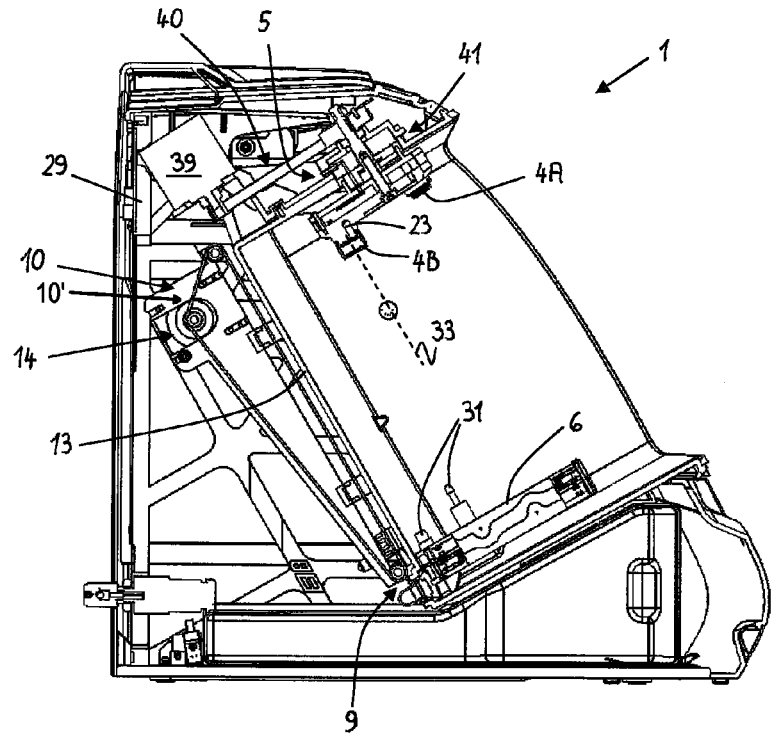
FIG. 2A shows a sectional diagram through the cleaning or care device of FIG. 1 without instruments connected to the connecting devices.
Figure 2B:
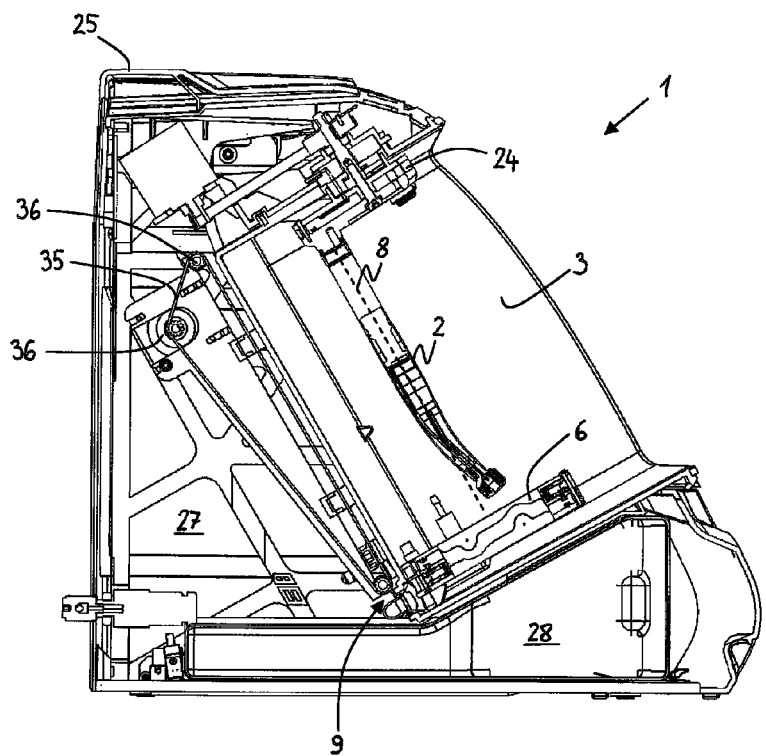
FIG. 2B shows the same sectional diagram as that in FIG. 2A but with an instrument connected to a connecting device.

The cleaning or care device 1 shown in FIGS. 1, 2A and 2B comprises an outer housing 25 which is made preferably of plastic and has a bottom plate, several side walls and a top plate. One of the side walls has a movable door, in particular a pivotable door or a movable cover, in particular a pivotable cover, preferably movable by means of hinges on the top plate. A cleaning or care chamber arranged in the interior of the housing 25 or a cleaning or care space 3 arranged in the interior of the housing 25 can be closed with the cover, and several couplings or connecting devices, namely in the present case three connecting devices 4A, 4B, 4C for medical, in particular dental instruments 2 that are to be cleaned or cared for are provided in this chamber or space 3. By means of the connecting devices 4A, 4B, 4C and one or more channels 23 provided therein, one or more cleaning or care media are delivered into the interior of the instruments 2. In addition a frame 6 with at least one nozzle 7 by means of which one or more cleaning or care media can be dispensed onto the outside of the instruments 2 is provided in the cleaning or care space 3. The at least one nozzle 7 is thus arranged separately from the connecting devices 4A, 4B, 4C and can be supplied with a cleaning and/or care medium independently of the connecting devices 4A, 4B, 4C, in particular temporally independently of the connecting devices 4A, 4B, 4C.

The cleaning or care space 3 is separated from a control space 27 (see FIG. 2B) by a wall 13 arranged in the interior of the cleaning or care device 1. A plurality of control and function elements of the cleaning or care device 1 are provided in or on the control space 27, for example, a supply or delivery device 5 which may contain among other things connections to one or more fluid sources, for example, to containers for cleaning media, care media or lubricants or to an external compressed air source and/or water source, lines for delivering the fluids, cleaning media, care media or lubricants, pumps, control and adjustment means, for example, valves, throttles, sensors, for example, for the flow measurement, concentration measurement, mixers and many other components. In addition to the delivery device 5, additional components, for example, containers for cleaning media, care media or lubricants or receptacles for such containers, a connection to an energy source, a drain tray 28 or a drain for spent cleaning media or care media, a control unit 29 for controlling and/or regulating the cleaning or care procedures, a memory unit, an operating display or an operating panel for the user are provided in or on the control space 27.

Figure 3:
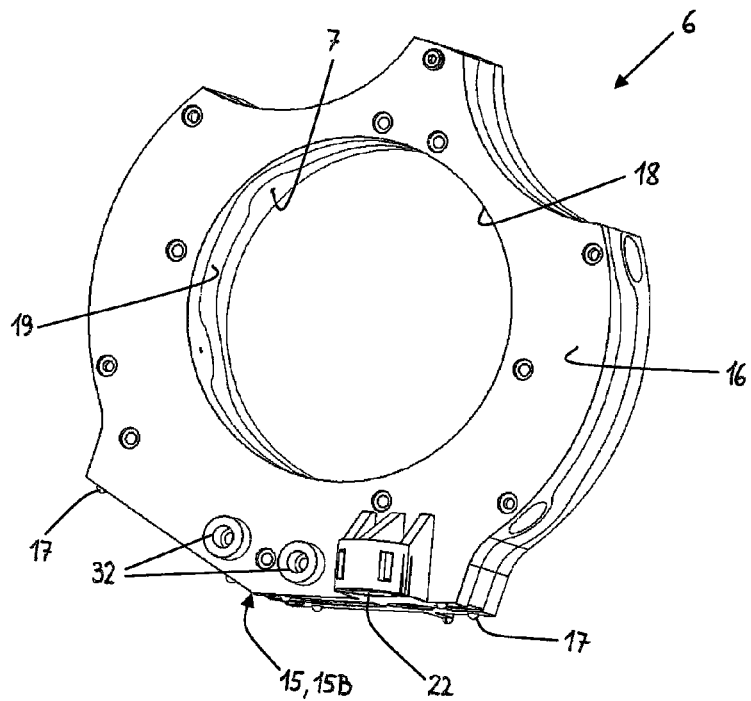
FIG. 3 shows an outer view of one embodiment of a frame that is movable by means of a magnetic coupling device.

The connecting devices 4A, 4B, 4C or at least parts thereof, the frame 6 and at least one flexible line tubing 30 connected to the frame 6 are accommodated in the cleaning or care room 3 (see FIG. 1). The flexible line tubing 30 is part of the delivery device 5 or is connected to it and conducts one or more cleaning or care media to the frame 6. On one of its two ends, the line tubing 30 is connected to a first connecting element 31, which is provided on a wall of the cleaning or care space 3 and which receives a cleaning or care medium from lines arranged in the control space 27 and conducts it to the line tubing 30. On its other end, the second end, the line tubing 30 is connected to a second connecting element 32 which is arranged on the frame 6 and which receives the cleaning or care medium from the line tubing 30 and transfers it to the frame 6. The two connecting elements 31, 32 are designed as pipe connections or bushings, for example, and are detachably connected to the line tubing 30 by plug connections. As shown in FIGS. 2A, 2B and 3, it is of course also possible to provide multiple connecting elements 31, 32, wherein each connecting element 31 is connected to a connecting element 32 via a line tubing 30, respectively, so that several separate supply pathways for cleaning or care media to the frame 6 are formed.

To be able to clean or care for the instruments 2 especially thoroughly, the frame 6 is movably accommodated in the cleaning or care space 3. The frame 6 is designed to move along a wall 13 of the cleaning or care space 3 and/or in relation to the connecting device 4A, 4B, 4C and/or along a longitudinal axis 8 of an instrument 2 connected to a connecting device 4A, 4B, 4C and/or along the longitudinal axis 33 of a connecting device 4A, 4B, 4C and/or along the extension of the longitudinal axis 33 (into the cleaning or care space 3) of the at least one connecting device 4A, 4B, 4C.

The movement of the frame 6 is induced by a magnetic coupling device 9 which transfers a drive movement of a drive device 10 arranged in the control space 27 to the frame 6. The magnetic coupling device 9 consists of two parts, one part being connected to the drive device 10 and arranged in the control space 27 and a second part being connected to the frame 6. The two parts of the magnetic coupling device 9 are separated from one another in space by a wall 13 of the cleaning or care space 3 but are arranged in the cleaning or care space 3 in such a way that they are magnetically coupled to one another.

The part of the magnetic coupling device 9 arranged in the control space 27 comprises at least one, and possibly several, first magnetic elements 11 which are attached in or on a magnet holding device 34. The first magnetic element 11 is preferably arranged close to the wall 13 or directly adjacent to the wall 13. The magnet holding device 34 is, for example, made of plastic and surrounds the first magnetic element 11 at least partially. The magnet holding device 34 preferably also serves as a connecting piece to the drive device 10, but of course a separate connecting piece may also be provided for it.

According to one embodiment, the drive device 10 for the first magnetic element 11 comprises a linear drive or translation movement generating drive 10', which moves the first magnetic element 11 substantially along at least a part of the wall 13. The drive device 10 for the first magnet element 11 is connected to a motor, for example, an electric motor, in particular a stepping motor whose driving movement is transferred to the first magnetic element 11. The driving movement is transferred according to the embodiments of FIGS. 2A, 2B by way of a belt drive 14 but it may also be accomplished by any other known approach, for example, by rotation of a threaded rod to which the first magnetic element 11 is attached.

The belt drive 14 comprises a belt 35, in particular a toothed belt to which the first magnetic element 11 is attached, for example, via the magnet holding device 34. The belt 35 runs over two or more pulleys 36, one pulley 36 being connected to the motor via a shaft and set in rotation by this shaft. The part of the belt 35 to which the first magnetic element is attached extends along the wall 13 of the cleaning or care space 3, in particular essentially parallel to the wall 13. As soon as the motor is activated, the first magnetic element 11 is thus moved along the wall 13. The control unit 29 controls the motor in such a way that it reverses the direction of rotation or the control unit 29 stops the motor as soon as the first magnetic element 11 has reached an end point on its path along the wall 13. An end point may be defined, for example, by a pulley 36 or by any other point beyond which the first magnetic element 11 or the second magnetic element 12 which, is magnetically coupled to the magnetic element of the frame(s) 6, should not move.

Figure 4:
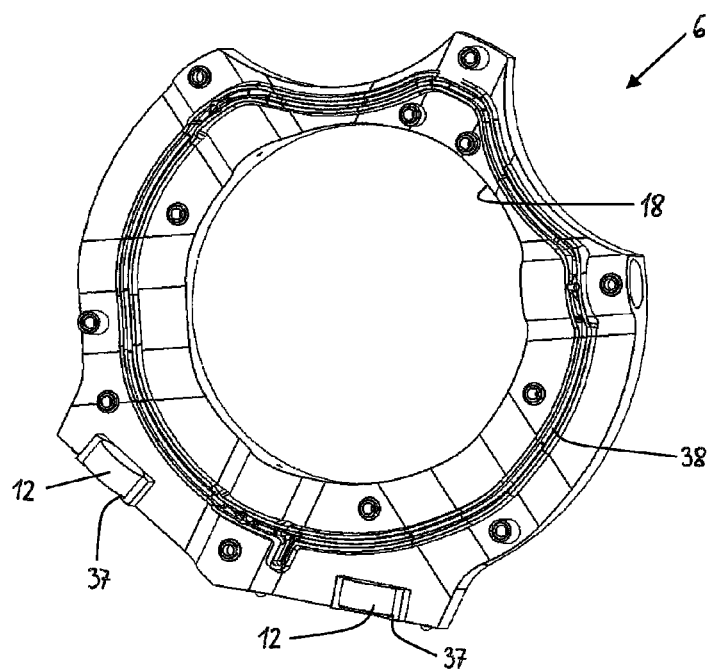
FIG. 4 shows a longitudinal section through the frame of FIG. 3.

The second part of the magnetic coupling device 9 which is connected to the frame 6 comprises at least one, and possibly several, second magnetic elements 12 which are arranged in receptacles or recesses 37 in the frame 6 (see FIG. 4). The second magnetic elements 12 are preferably arranged close to the wall 13 or immediately adjacent to the wall 13 on which the first magnetic element 11 is also positioned (on the opposite side). The second magnetic elements 12 are in particular arranged on a side or area of the frame 6 facing the wall 13 of the cleaning or care space 3 on which the first magnetic element 11 is also positioned (on the opposite side). Especially good magnetic coupling of the magnetic elements 11, 12 is thus achieved. If the first magnetic element 11 moves along the wall 13 as described already above, then the second magnetic element 12 and thus the entire frame 6 follow this movement of the first magnetic element 11 because of the magnetic coupling of the magnetic elements 11, 12. Thereby the frame 6 at least partially contacts the wall 13.

To achieve an easy movement on or along the wall 13 of the cleaning or care space 3, the frame 6 has a plurality of protrusions 17 which are designed as noses or hemispherical or bulging protrusions. The protrusions 17 are preferably arranged on the side or surface of the frame 6 on which the second magnetic elements 12 or their receptacles 37 are provided. Because of these protrusions 17, it is less than the entire side or surface of the frame 6 on which the second magnetic elements 12 are arranged that slides along the wall 13.

For centering and guiding the frame 6 along the wall 13, a guide device 15 is provided on the frame 6 and on the wall 13, in particular on the side or surface of the frame 6 on which the second magnetic elements 12 or their receptacles 37 are provided. The guide device 15 has corresponding geometric shapes on the frame 6 and on the wall 13 which are designed, for example, as sections of a side wall of the frame 6 and the wall 13 arranged at an angle to one another and which form a point or edge 15B in the contact area (see FIG. 3) and from a corresponding angle 15A (see FIG. 1). If the frame 6 moves along the wall 13, then the edge 15B is guided in the angle 15A. The guide device 15 may of course also have other geometric shapes, for example, rails which are accommodated and guided in corresponding recesses.

Figure 5:
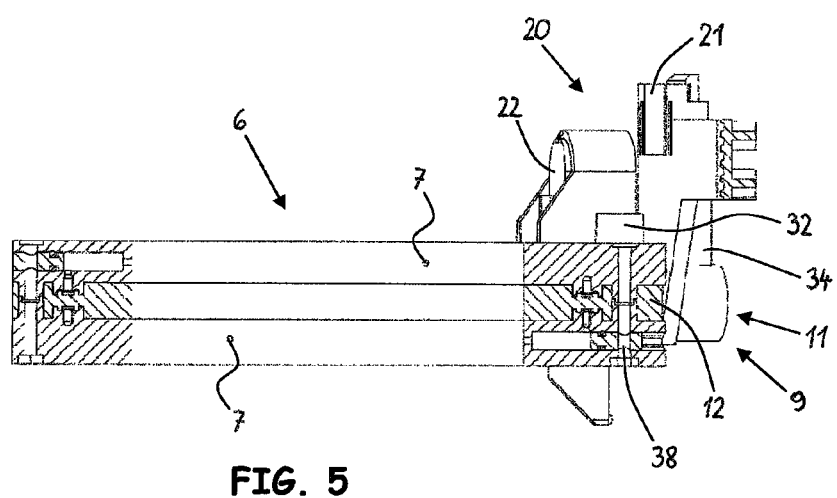
FIG. 5 shows a cross section through the frame of FIG. 3.

As shown in FIG. 5 in particular, a third magnetic element 22 which is part of a detection device 20 for detecting a relative movement between the frame 6 and the first magnetic element 11 is provided on the frame 6. Such a relative movement occurs, for example, when the frame 6 is not being moved by the first magnetic element 11 or is not being moved jointly with the first magnetic element 11. The detection device 20 additionally includes a magnetic sensor 21 which is movable jointly with the first magnetic element 11 arranged outside of the cleaning or care space 3 and which is operatively connected to the magnetic element 22 provided on the frame 6. The magnetic sensor 21, for example, a Hall sensor or a Reed sensor, is preferably attached to the magnet holding device 34. The magnetic sensor 21 detects the magnetic field of the third magnetic element 22. If the magnetic sensor 21 moves away from the third magnetic element 22, the magnetic sensor 21 no longer detects its magnetic field or the magnetic sensor 21 detects the decline in the magnetic field strength. In both cases the magnetic sensor 21 sends a signal to the control unit 29, which informs the user of the relative movement between the frame 6 and the first magnetic element 11, for example, by means of an optical or acoustic warning device and/or interrupts or suppresses the operation of the cleaning or care device. The magnetic sensor 21 and the third magnetic element 22 are arranged close to one another, in particular close to the wall 13. The third magnetic element 22 is preferably arranged on or near the side or surface of the frame 6 where the second magnetic element 12 or its receptacles 37 are provided. According to an alternative embodiment the magnetic sensor 21 detects the second magnetic element 12 so that no third magnetic element 22 is needed.

One or more channels or lines 38 pass through the body 16 of the frame 6, each being connected to at least one connecting element 32 in order to conduct a cleaning or care medium from the connecting element 32 to the nozzles 7. The nozzles 7, i.e., the nozzle openings are provided on an inside wall 19 of a through-bore 18 passing through the body 16. The through-bore 18 is designed as a closed bore, in particular a circular borehole whose diameter is preferably of such a size that only a single instrument 2 which is to be cleaned can find space therein. Accordingly the nozzles 7 are always directed only at one instrument 2 during the cleaning or care procedure and dispense a cleaning or care medium only to this instrument 2 (directly).

The body 16 of the frame 6 preferably consists of several layers or strata in which or on whose adjacent surfaces the lines 38 are provided. According to the embodiment shown in FIG. 5 the frame 6 consists of three layers, wherein the two outer layers are made of plastic and the middle layer is designed as a sealing element and is made of a material having a higher elasticity than the two outer layers, for example, rubber.

Finally, FIGS. 1, 2A and 2B show that the three connecting devices 4A, 4B, 4C are arranged on a shared base element 24 which is arranged rotatably in the cleaning or care device 1. Due to the rotatability of the base element 24 the three connecting devices 4A, 4B, 4C are movable in relation to the frame 6, i.e., they are rotatable. In particular the three connecting devices 4A, 4B, 4C are rotatable in relation to the frame 6 and/or the three connecting devices 4A, 4B, 4C can be arranged in a predetermined stopped position and/or the frame 6 and the base element 24 can be arranged relative to one another by rotation of the base element 24 so that only one instrument 2 to be cleaned and/or only one connecting device 4A, 4B, 4C is arranged (directly) opposite the through-bore 18 in the frame 6. If the diameter of the through-bore 18 is such that only a single instrument 2 to be cleaned can be accommodated therein, then as soon as the frame 6 moves along a longitudinal axis 8 of the instrument 2, only this instrument 2 accommodated in the through-bore 18 is supplied (directly) by the nozzles 7 with a cleaning or care medium. The exterior cleaning or care of the instruments 2 thus takes place sequentially.

A cleaning or care device with a rotary base element on which several connecting devices are arranged is also known from the European patent application EP 10155736.1, the content of which is completely included in the present patent application. The cleaning or care device according to the patent application EP 10155736.1 has a single delivery device for the cleaning or care media, to which only one of the connecting devices is connected by turning the base part, while none of the other connecting devices are connected to the delivery device, so that only one instrument at a time can be supplied with a cleaning or care medium for internal cleaning.

Accordingly, in a preferred embodiment, the base element 24 including the three connecting devices 4A, 4B, 4C and the delivery device 5 of the present cleaning or care device 1 are also movable in relation to one another, such that (selectively) only one of the connecting devices 4A, 4B, 4C is connected to the delivery device 5 and can be supplied with a cleaning and/or care medium for the internal cleaning of an instrument 2, while the other connecting devices 4A, 4B, 4C are not connected to the delivery device 5 and cannot be supplied with a cleaning and/or care medium. The cleaning or care device 1 thus has a single delivery device 5, to which only one of the connecting devices 4A, 4B, 4C and/or its channel 23 is connected, whereas all the other connecting devices 4A, 4B, 4C are not connected to the delivery device 5, so that only one instrument 2 can be supplied with a cleaning or care medium for internal cleaning. In particular the cleaning or care device 1 or the delivery device 5 comprises a single interface or transfer point for selective coupling or connection to one of the connecting devices 4A, 4B, 4C to which the cleaning or care media are transferred. Several lines for cleaning or care media can clearly be provided or combined at this interface. The interface preferably has at least one opening for a cleaning fluid and at least one opening for a lubricant.

With such a cleaning or care device 1, both the external cleaning and care of the instruments 2 as well as the internal cleaning or care of the instruments 2 are performed sequentially, wherein according to one embodiment, the external and internal cleaning/care are performed on a first instrument 2, and then the base element 24 rotates, so that then the external and internal cleaning/care is/are performed on a second or additional instrument 2. Alternatively, one of the two cleaning/care treatments (internal cleaning or care/external cleaning or care) is performed first on all instruments 2, and then the other of the two cleaning/care treatments (internal cleaning or care/external cleaning or care) is performed. Preferably first the internal cleaning or care is performed on all instruments and then the external cleaning or care is performed on all instruments 2, thereby significantly reducing the risk of cross-contamination between the instruments 2. Especially preferably the position in which an instrument 2 to be cleaned is arranged (directly) opposite the through-bore 18 in the frame 6 is the same as the position in which the connecting device 4A, 4B, 4C, to which this instrument 2 that is opposite the through-bore 18 is connected, is connected to the delivery device 5.

A drive motor 39 is preferably provided in the cleaning or care device 1 for the relative movement of the connecting devices 4A, 4B, 4C or of the base element 24. The drive motor 39 is arranged outside of the cleaning or care space 3. It comprises, for example, an electric motor, in particular a stepping motor. The use of a stepping motor is particularly advantageous for the present application because of its reliability and simple control. The drive motor 39 is preferably connected to the connecting devices 4A, 4B, 4C and/or the base element 24 via at least one drive element, for example, a belt drive 40 and/or a shaft.

The cleaning or care device 1 additionally comprises a distributor element 41 that is provided between the movable or rotary base element 24 and the delivery device 5 for guiding a cleaning and/or care medium from the delivery device 5 to the connecting devices 4A, 4B, 4C, wherein the distributor element 41 has a first distributor part that is movable with the base element 24 in relation to the delivery device 5 and a second distributor part that is fixed in relation to the delivery device 5. This design ensures a particularly reliable transfer of the cleaning and/or care medium to the base element 24. The first distributor part preferably has at least one separate line or one separate line segment for each of the connecting devices 4A, 4B, 4C. The second distributor piece comprises at least one line for a cleaning and/or care medium, wherein the lines of the first distributor part can be connected to the at least one line of the second distributor part through the movement of the base element 24 and thus of the first distributor part in relation to the second distributor part. Thus the cleaning or care media for the internal cleaning of the instruments 2 is transferred via this fluid-conducting connection from the delivery device 5 to the connecting devices 4A, 4B, 4C and into the interior of the instruments 2 to be cleaned, which are coupled to the connecting devices 4A, 4B, 4C. The first and second distributor parts are preferably disk shaped.

The cleaning or care device 1 preferably comprises a detection unit for determining which of the connecting devices 4A, 4B, 4C is occupied by an instrument 2 and/or which of the connecting devices 4A, 4B, 4C is not occupied by an instrument 2 and for delivering corresponding occupation signals for each connecting device 4A, 4B, 4C. The detection unit is connected to the control unit 29, which is designed to supply cleaning or care media on the basis of the occupation signals delivered by the detection unit only those connecting devices 4A, 4B, 4C to which an instrument 2 is connected. The detection unit consists, for example, of a radiation source, in particular a light source that emits radiation into the cleaning or care space 3, and an optical sensor, that detects an attenuation or interruption in a radiation emitted into the cleaning or care space 3 due to an instrument 2 coupled to the connection. If one of the connecting devices 4A, 4B, 4C is empty, i.e., not occupied by an instrument 2, then according to a preferred embodiment, the control unit 29 operates the drive motor 39 so that it does not stop when the empty connecting device 4A, 4B, 4C is connected to the delivery device 5, but instead it continues to run, so that the base element 24 is moved further, until the next connecting device 4A, 4B, 4C occupied by an instrument 2 is connected to the delivery device 5.

The invention is not limited to the embodiment described here, but instead includes all embodiments which employ or comprise the corresponding basic function principle of the invention. In addition, all the features of all the embodiments described and illustrated here can be combined with one another.

What is claimed is:

1. A cleaning or care device for medical or dental instruments comprising:
   an outer housing defining an interior,
   a wall arranged in the interior of the outer housing, said wall separating a cleaning or care space from a control space,
   at least one connecting device which is arranged in the cleaning or care space and to which an instrument to be cleaned can be connected,
   a delivery device for delivery of at least one cleaning or care medium, wherein the delivery device comprises a frame, on which at least one nozzle is provided for dispensing a cleaning or care medium on the outside of the instrument to be cleaned, wherein the frame is arranged in the cleaning or care space and can be moved in relation to the at least one connecting device, to essentially follow a longitudinal axis of an instrument connected to the at least one connecting device, and
   a magnetic coupling device, which transmits a driving movement generated outside of the cleaning or care space to the frame for moving the frame in relation to the at least one connecting device, wherein
   the magnetic coupling device comprises at least one first magnetic element arranged in the control space in the interior of the outer housing and at least one second magnetic element coupled to the frame and arranged in the cleaning or care space in the interior of the outer housing, wherein the at least one first magnetic element and the at least one second magnetic element are magnetically coupled to each other and are movable relative to the outer housing to move the frame in relation to the at least one connecting device.

2. The cleaning or care device according to claim 1, wherein
   the at least one first magnetic element is coupled to a motor drive device.

3. The cleaning or care device according to claim 1, wherein
   the at least one second magnetic element is arranged in a receptacle or recess in the frame.

4. The cleaning or care device according to claim 2, wherein
   the motor drive device coupled to the first magnetic element comprises a linear drive or translational movement generating drive that moves the first magnetic element along a wall of the cleaning or care space.

5. The cleaning or care device according to claim 2, wherein
   the motor drive device coupled to the first magnetic element comprises a belt drive.

6. The cleaning or care device according to claim 1, wherein
   a guide device for guiding the frame along the wall of the cleaning or care space is provided on the frame and/or on a wall of the cleaning or care space.

7. The cleaning or care device according to claim 1, wherein
   the frame has one or more protrusions protruding away from the body of the frame, the protrusions being positionable to serve as sliding contact surfaces with a wall of the cleaning or care space.

8. The cleaning or care device according to claim 1, wherein
the body of the frame has a through-bore, in which an instrument to be cleaned can be accommodated, wherein multiple nozzles are arranged on the inside wall of the through-bore.

9. The cleaning or care device according to claim 1, comprising
a detection device for detecting a relative movement between the frame and the first magnetic element.

10. The cleaning or care device according to claim 9, wherein
the detection device comprises a magnetic sensor, which is movable jointly with the first magnetic element arranged outside of the cleaning or care space and which is operatively connected to a magnetic element provided on the frame.

11. The cleaning or care device according to claim 1, wherein
the at least one connecting device has a channel connected to the delivery device by which a cleaning or care medium can be delivered into the interior of an instrument.

12. The cleaning or care device according to claim 1, wherein
at least two connecting devices are provided for instruments to be cleaned, wherein the at least two connecting devices are movable relative to the frame such that only one of the connecting devices is opposite a through-bore in the frame, on which the at least one nozzle for dispensing a cleaning or care medium is provided.

13. The cleaning or care device according to claim 12, wherein
the at least two connecting devices are arranged on a shared base element, which is arranged rotatably in the cleaning or care device.

14. A method for manufacturing a cleaning or care device, the cleaning or care device comprising:
an outer housing having in its interior a cleaning or care space and a control space,
at least one connecting device which is arranged in the cleaning or care space and to which an instrument to be cleaned can be connected, and a delivery device for delivery of at least one cleaning or care medium, wherein the delivery device comprises a frame, on which at least one nozzle is provided for dispensing a cleaning or care medium on the outside of the instrument to be cleaned, wherein the frame can be moved in relation to the at least one connecting device, to essentially follow a longitudinal axis of an instrument connected to the at least one connecting device,
the method comprising:
providing the cleaning or care device with a magnetic coupling device, which transfers a driving movement generated outside of the cleaning or care space to the frame for moving the frame relative to the at least one connecting device, wherein
the magnetic coupling device comprises at least one first magnetic element arranged in the control space in the interior of the outer housing and at least one second magnetic element coupled to the frame and arranged in the cleaning or care space in the interior of the outer housing, wherein the at least one first magnetic element and the at least one second magnetic element are magnetically coupled to each other and are movable relative to the outer housing to move the frame in relation to the at least one connecting device.

15. The method for manufacturing a cleaning or care device according to claim 14, further comprising:
providing at least two connecting devices for instruments to be cleaned, the connecting devices being movable relative to the frame such that only one of the connecting devices is opposite a through-bore in the frame, on which the at least one nozzle for dispensing a cleaning or care medium is provided.

* * * * *